United States Patent
Yaghi et al.

(10) Patent No.: US 10,766,908 B2
(45) Date of Patent: Sep. 8, 2020

(54) CALCIUM L-LACTATE FRAMEWORKS AS NATURALLY DEGRADABLE CARRIERS

(71) Applicant: The Regents of the University of California, Oakland, CA (US)

(72) Inventors: Omar M. Yaghi, Berkeley, CA (US); JingJing Yang, Berkeley, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 16/697,150

(22) Filed: Nov. 26, 2019

(65) Prior Publication Data
US 2020/0095264 A1   Mar. 26, 2020

Related U.S. Application Data

(63) Continuation of application No. PCT/US2018/035237, filed on May 31, 2018.

(60) Provisional application No. 62/513,973, filed on Jun. 1, 2017.

(51) Int. Cl.
| | |
|---|---|
| *C07F 3/00* | (2006.01) |
| *A01N 25/08* | (2006.01) |
| *A61K 8/02* | (2006.01) |
| *A61K 47/12* | (2006.01) |
| *A61Q 5/00* | (2006.01) |
| *A61Q 19/00* | (2006.01) |

(52) U.S. Cl.
CPC .............. *C07F 3/003* (2013.01); *A01N 25/08* (2013.01); *A61K 8/0216* (2013.01); *A61K 47/12* (2013.01); *A61Q 5/00* (2013.01); *A61Q 19/00* (2013.01)

(58) Field of Classification Search
CPC ....... C07F 3/003; A01N 25/08; A61K 8/0216; A61K 47/12; A61Q 5/00; A61Q 19/00
See application file for complete search history.

(56) References Cited

U.S. PATENT DOCUMENTS

| | | | | |
|---|---|---|---|---|
| 2013/0096210 | A1* | 4/2013 | Yaghi | B01J 20/226 514/784 |
| 2014/0012039 | A1* | 1/2014 | Yaghi | B01J 31/02 562/512.2 |
| 2016/0008472 | A1* | 1/2016 | Yaghi | C07F 5/025 424/499 |
| 2017/0081345 | A1* | 3/2017 | Yaghi | C01B 39/00 |
| 2017/0101429 | A1* | 4/2017 | Yaghi | F17C 11/00 |
| 2017/0145299 | A1* | 5/2017 | Schultheiss | C09K 8/03 |
| 2017/0166805 | A1* | 6/2017 | Schultheiss | C09K 8/03 |

OTHER PUBLICATIONS

Yang et al. Calcium L-Lactate Frameworks as Naturally Degradable Carriers for Pesticides. J. Am. Chem. Soc. 2017, 139, 8118-8121 (pub. date Jun. 4, 2017). (Year: 2017).*
Miller et al. A rare example of a porous Ca-MOF for the controlled release of biologically active NO†. Chem. Commun., 2013, 49, 7773-7775. (Year: 2013).*

* cited by examiner

*Primary Examiner* — Robert A Wax
*Assistant Examiner* — Olga V. Tcherkasskaya
(74) *Attorney, Agent, or Firm* — Richard Aron Osman

(57) ABSTRACT

Porous calcium lactate metal-organic frameworks (MOFs) comprise non-toxic metal ions—Ca(II) and non-toxic, renewable and cheap linkers—lactate and acetate. The MOFs are nontoxic and environmentally-benign, and can be used as degradable carriers.

18 Claims, 10 Drawing Sheets

CALCIUM L-LACTATE FRAMEWORKS AS NATURALLY DEGRADABLE CARRIERS

CROSS-REFERENCE TO RELATED APPLICATIONS

This application claim priority to U.S. Ser. No. 62/513,973, filed: Jun. 1, 2017.

INTRODUCTION

Metal-organic frameworks (MOFs) are porous, crystalline materials constructed by linking metal ions with organic structs.[1] The diverse number of ways the size, geometry, and functionality of the organic struts and the metal ions can be tuned has led to the discovery of more than 20,000 MOFs,[2] which allows a wide range of applications, most notably in gas separation, storage, and catalysis.[3] However, the vast majority of MOFs that have been made so far are based on transition metal ions and organic linkers derived from petrochemical sources, their intrinsic toxicity has precluded many of the important applications requiring eco-friendly (environment-friendly) materials, e.g. food industry, biomedical application, and agriculture.[4]

Preparation of MOFs from eco-friendly metal ions—$Ca^{2+}$, with non-toxic, naturally occurring linkers would permit these wider scope applications.[4,5] Though lots of attention have been focused on the area, no porous examples have been demonstrated to date. The challenge lies in both of the components: the poorly-defined coordination geometries and high coordination number of $Ca^{2+}$ metal ions, and the flexibility of naturally occurring organic linkers, which generally lead to dense structures.[4,6]

SUMMARY OF THE INVENTION

Disclosed are porous calcium lactate metal-organic frameworks (MOFs), made from non-toxic metal ions—Ca (II) and non-toxic, renewable and cheap linkers—lactate and acetate. The MOFs are environmentally-benign, and we demonstrate their use as a degradable solid carriers, including for pesticides, like volatile fumigants, showing that the MOFS not only prolong the effective time of the fumigants through slow release, but also degrade easily after implementation, leaving only fertilizer (Ca) in the soil.

In aspect the invention provides a $Ca^{2+}$-based metal-organic framework (MOF) composition comprising chelating L-lactate and acetate, of formula:

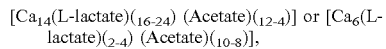

[Ca$_{14}$(L-lactate)$_{(16-24)}$ (Acetate)$_{(12-4)}$] or [Ca$_6$(L-lactate)$_{(2-4)}$ (Acetate)$_{(10-8)}$], wherein the lactate and acetate sum to 28 and 12, respectively.

In embodiments the invention provides:
the formula is: [Ca$_{14}$(L-lactate)$_{(18)}$ (Acetate)$_{(10)}$], [Ca$_{14}$(L-lactate)$_{(21)}$ (Acetate)$_{(7)}$], [Ca$_6$(L-lactate)$_{(4)}$ (Acetate)$_{(8)}$], or [Ca$_6$(L-lactate)$_{(2.5)}$ (Acetate)$_{(9.5)}$];
the MOF is of formula: [Ca$_{14}$(L-lactate)$_{(20)}$ (Acetate)$_{(8)}$] (MOF-1201);
the MOF is of formula: [Ca$_6$(L-lactate)$_{(3)}$ (Acetate)$_{(9)}$] (MOF-1203);
the composition comprises an agent encapsulated in the MOF, such as wherein the agent is selected from:
a crop protection product, such as a fertilizer (e.g. nitrogenous, phosphate, potassium, or calcium fertilizer) or pesticide (e.g. insecticide, herbicide, fungicide), which may be a fumigant or sprayable formulation;
a drug or therapeutic agent, such as an antimicrobial (e.g. antibacterial, antiviral or antifungal) agent, dermatological or skin or hair care agent, etc.
an aroma compound, such as an odorant, aroma, fragrance or perfume including essential oil, extracts, synthetic odorants; and
a food additive, such as acidulents and acidity regulators, anticaking agents, antifoaming and foaming agents, antioxidants like ascorbic acid, colorings and color retention agents, fortifying agents like vitamins, minerals, and micronutrients, emulsifiers, flavorings and flavor enhancers, glazing agents, preservatives, stabilizers, thickeners and gelling agents, natural and artificial sweeteners and thickeners.

In an aspect the invention provides a method of delivering or distributing an agent in a non-toxic, biodegradable carrier, the method comprising delivering or distributing the agent encapsulated in a subject composition.

The invention encompasses all combination of the particular embodiments recited herein, as if each combination had been laboriously recited.

DESCRIPTION OF PARTICULAR EMBODIMENTS OF THE INVENTION

Unless contraindicated or noted otherwise, in these descriptions and throughout this specification, the terms "a" and "an" mean one or more, the term "or" means and/or and polypeptide sequences are understood to encompass opposite strands as well as alternative backbones described herein.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein, including citations therein, are hereby incorporated by reference in their entirety for all purposes.

We exemplify the synthesis of eco-friendly MOFs including: MOF-1201 [$Ca_{14}$(L-lactate)$_{20}$(Acetate)$_8$($C_2H_5OH$) ($H_2O$)] and MOF-1203 [$Ca_6$(L-lactate)$_3$(Acetate)$_9$($H_2O$)], based on $Ca^{2+}$ ions and innocuous lactate and acetate linkers,[7] both show permanent porosity. We suspect the key to our success in assembling MOF-1201 and 1203 lies in the choice of linkers—the chelating lactate and acetate, which allows the formation of rigid calcium oxide linked polyhedra ($Ca^{2+}$ as nodes and O from lactate or acetate as bridges), and then the construction of 3D extended open frameworks based on these polyhedra. We also demonstrate using the MOFs as carriers, e.g. for the slow release of fumigant cis-1,3-dichloropropene. The ready degradability provides first examples of porous carriers for fumigants that can decompose in water.

Hydrothermal reaction of a suspension of calcium acetate and L-lactic acid in ethanol (methanol) at 120° C. (100° C.) for a period of 4 (3) days gave colorless rod-shaped crystals of MOF-1201 (needle-shaped crystals of MOF-1203), respectively. The crystals were then harvested for single-crystal X-ray diffraction analysis. The exact molar ratios of the lactate and acetate linkers in the MOFs were further determined by $^1$H-NMR spectroscopy and elemental microanalysis of the solvent-free samples [see the Supporting Information (SI), section S1].

Figure 1A:
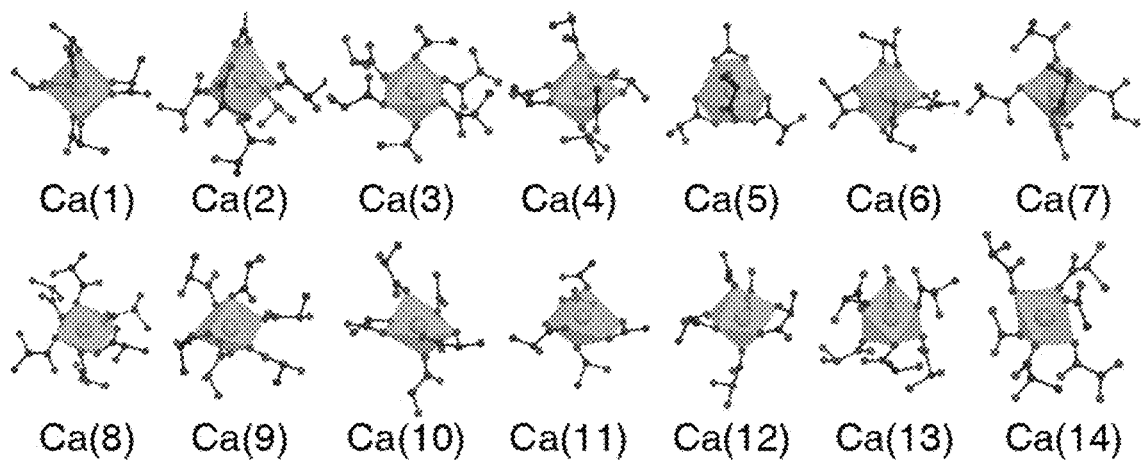
FIG. 1a. All distinct $Ca^{2+}$ centers exist in MOF-1201 and their coordination with lactate and acetate. Coordination numbers for Ca(1) to Ca(14) are 8, 7, 6, 7, 9, 8, 7, 7, 7, 7, 8, 7, 7, and 6, respectively.

Single-crystal X-ray diffraction analysis revealed that both MOF-1201 and 1203 are extended frameworks constructed from $Ca^{2+}$ as nodes and lactate and acetate as linkers. MOF-1201 crystallizes in the monoclinic $P2_1$ space group with the lattice constant of a=24.39 Å, b=13.26 Å, c=24.97 Å, β=90.33°. In this structure, fourteen crystallographically unique calcium atoms exist [Ca(1) to Ca(14)] (FIG. 1a), all of which are capped by the O atoms from lactate (carboxylic O or hydroxyl O), acetate (carboxylic O) or water to form calcium oxide polyhedra. Coordination modes of the linkers vary across metal centers—four different modes are found in lactate [(i), (ii), (iii), and (vi)] and three in acetate [(vii), (ix), and (xi)] (FIG. 1c), among which the lactate with mode (vi) and the acetate with mode (vii) act as terminal ligands and cap only one $Ca^{2+}$ center [Ca(5), and Ca(11), respectively], whilst others act as bridges to connect two or three $Ca^{2+}$. In the asymmetric unit, Ca(1), Ca(2), and Ca(3) are bridged by a lactate with coordination mode (i)—Ca(1) coordinates to the hydroxyl O and the adjacent carboxylic O, Ca(2) coordinates to only the carboxylic O, and Ca(3) coordinates to the other carboxylic O (FIG. 2a, left column) Similarly, Ca(1), Ca(2), and Ca(4) are bridged by the same mode; Ca(4), Ca(5), and Ca(7) are bridged by mode (iii); Ca(7), Ca(8), and Ca(9) by mode (i); Ca(7), Ca(8), and Ca(10) by mode (i); Ca(10), Ca(11), and Ca(12) by mode (xi); Ca(6), Ca(5), and Ca(7) by mode (ii); Ca(6), Ca(13), and Ca(14) by mode (i) to connect all of the $Ca^{2+}$ centers.

The resultant extended framework of MOF-1201 possesses 1D infinite channels along b axis (FIG. 2a, middle column) The channels are constructed from a right-handed single strand helical chain (FIG. 2a, right column), with sixteen $Ca^{2+}$ atoms per turn [in the sequence of Ca(4), Ca(2), Ca(1), Ca(11), Ca(12), Ca(13), Ca(6), Ca(5), Ca(4), Ca(2), Ca(1), Ca(11), Ca(12), Ca(13), Ca(6), and Ca(5)]. The aperture is around 7.8 Å and the pitch is around 13.3 Å. Two adjacent turns are further crosslinked by extra calcium oxide polyhedra. Specifically, the two Ca(2) and two Ca(13) centers in each turn are bridged by three calcium oxide polyhedra (in the sequence of Ca(3)-Ca(2)-Ca(3), and Ca(14)-Ca(13)-Ca(14)). The two Ca(5) and two Ca(11) in each turn are bridged by seven calcium oxide polyhedra [in the sequence of Ca(7)-Ca(8)-Ca(9)-Ca(8)-Ca(9)-Ca(8)-Ca (7), and Ca(10)-Ca(8)-Ca(9)-Ca(8)-Ca(9)-Ca(8)-Ca(10)]. The curved bridges result in a slightly larger internal pore size (c.a. 9.6 Å) compared to the aperture.

Figure 2A:
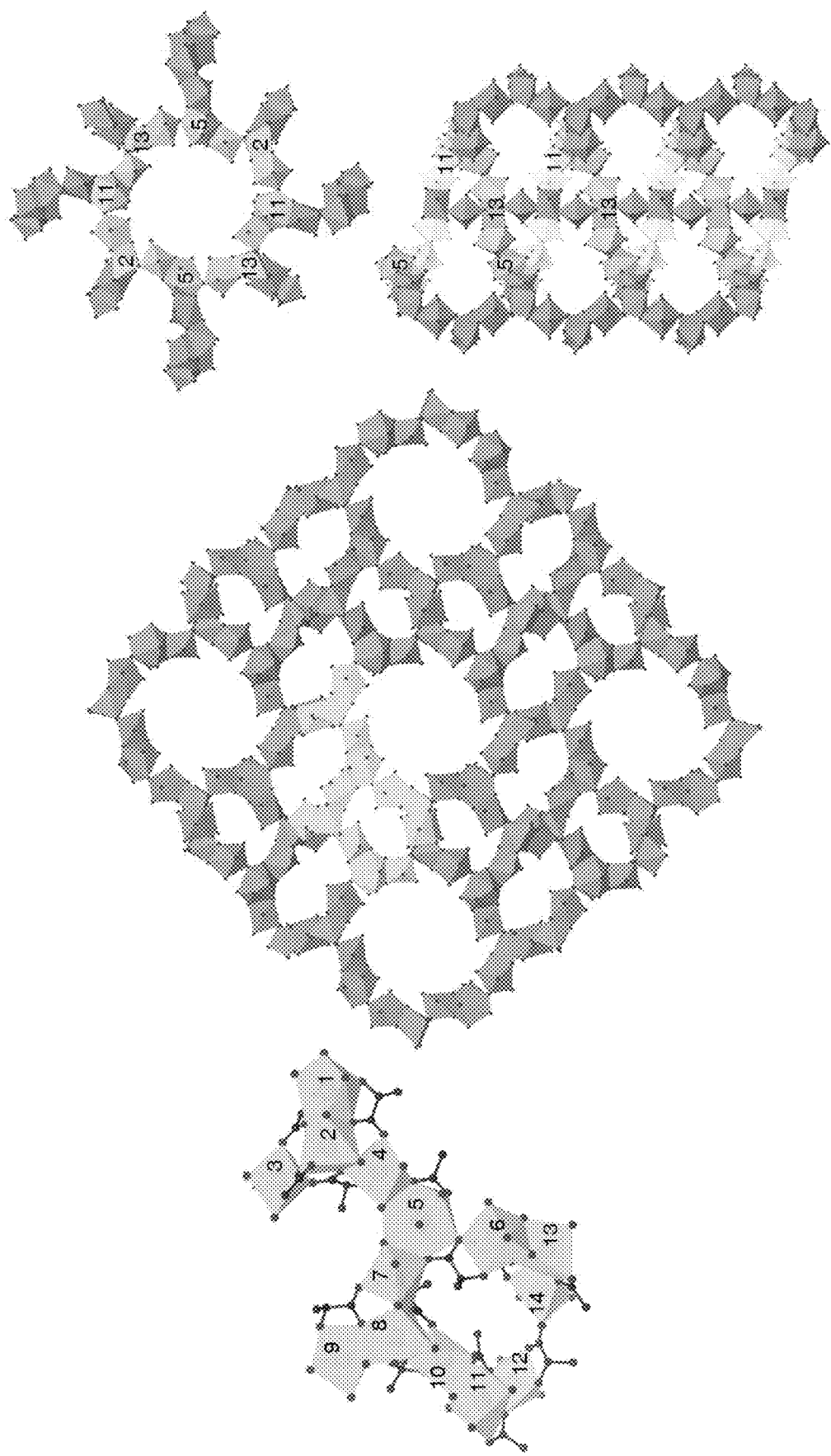
FIG. 2a. Left column: asymmetric unit in MOF-1201 as shown in ball-and-stick diagram; second column: overall structures viewed along b axis represented in calcium oxide polyhedral; right column, channels viewed along b axis (top) and a axis (bottom).

In FIG. 2a first column the asymmetric unit in MOF-1201 is shown in a ball-and-stick diagram, ligands who partially connect to symmetry generated $Ca^{2+}$ centers are omitted for clarity; more than one bridge could exist for the same set of $Ca^{2+}$ centers; second column overall structures viewed along b axis represented in calcium oxide polyhedra. Asymmetric units are highlighted, and open channels are shown; right column, channels viewed along b axis (top) and a axis (bottom). Calcium oxide polyhedra belonging to aperture are highlighted. In color, as shown in priority application, C in black, O in red, Ca in cyan, $Ca^{2+}$ oxide polyhedra in cyan, H omitted for clarity.

Figure 1B:
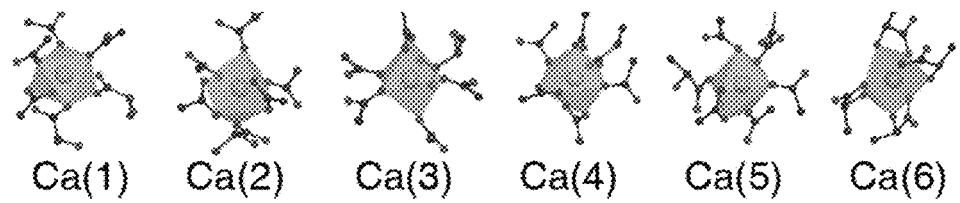
FIG. 1b. All distinct $Ca^{2+}$ centers exist in MOF-1203 and their coordination with lactate and acetate. Coordination numbers for Ca(1) to Ca(6) are 7, 8, 7, 8, 7, and 9, respectively.
Figure 1C:
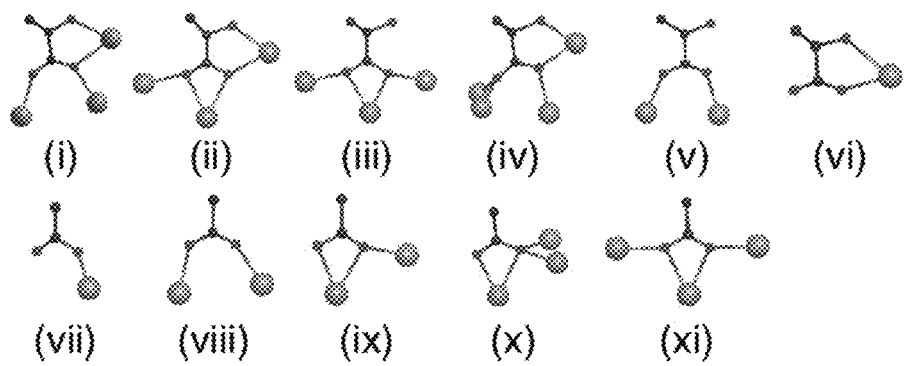
FIG. 1c. Coordination modes of the lactate [(i)-(vi)] and acetate [(vii)-(xi)]. C in black, O in red, Ca in cyan, $Ca^{2+}$ oxide polyhedra in cyan, H omitted for clarity.

The other MOF-1203, crystallized in the orthorhombic $I2_12_12_1$ space group, has a lattice constant of a=10.50 Å, b=22.26 Å, c=31.25 Å. Six distinct $Ca^{2+}$ centers exist in the structure, and are linked by lactate and acetate to form linked calcium oxide polyhedra (FIG. 1b). Three coordination modes are found in lactate [(i), (iv), and (v)] and in acetate [(viii), (x), and (xi)] (FIG. 1c), all linkers act as bridges connecting two to four $Ca^{2+}$ centers. In the asymmetric unit, Ca(1), Ca(2), Ca(3), and Ca(6) are bridged by a lactate with coordination mode (iv)—Ca(6) coordinates to the hydroxyl O and the adjacent carboxylic O, Ca(1) coordinates to only the carboxylic O, and Ca(2) and Ca(3) coordinate to the other carboxylic O (FIG. 2b, left column) Ca(3), Ca(4), and Ca(5) are bridged by an acetate with mode (xi). The resultant extended framework reveals another type of 1D open channel, which has an aperture made from 22 calcium oxide polyhedra. However, the aperture size is smaller than MOF- 1201 as the result of its rectangular shape, and the two incurvate Ca(4) further divided the aperture into two smaller ones (c.a. 4.6 Å).

Figure 2B:
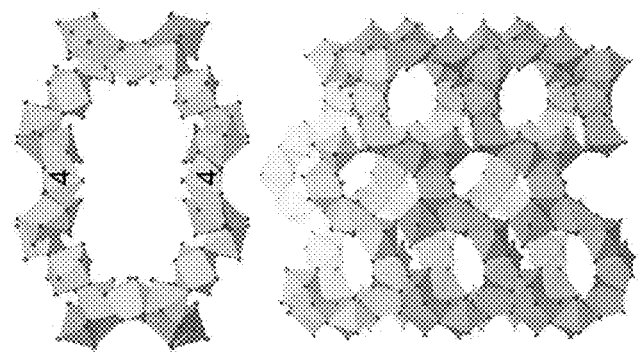
FIG. 2b. First column: asymmetric unit in MOF-1203 as shown in ball-and-stick diagram; second column: overall structures viewed along a axis represented in calcium oxide polyhedra; right column, channels viewed along a axis (top) and [01$\bar{1}$] direction (bottom).
Figure 2B:
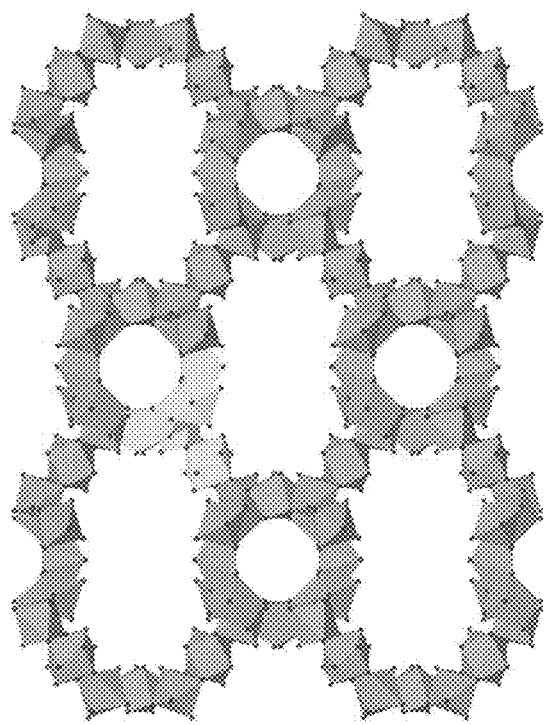
Figure 2B:
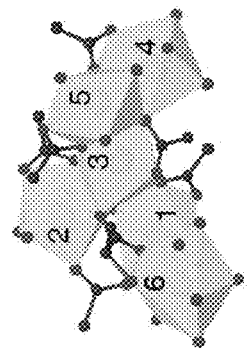
Figure 3A:
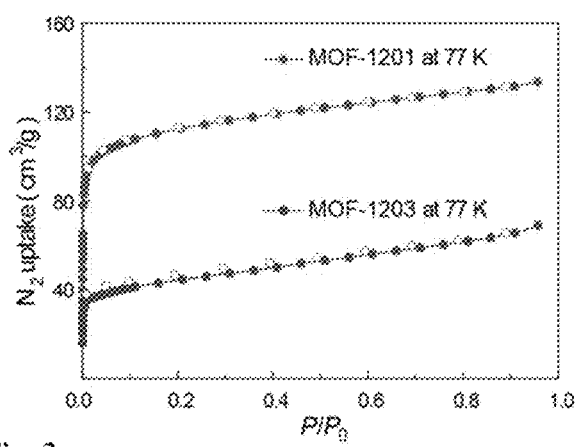
FIG. 3a. Nitrogen sorption isotherms of MOF-1201 and 1203 at 77 K, solid and open circles represent the adsorption and desorption branches, respectively.
Figure 3B:
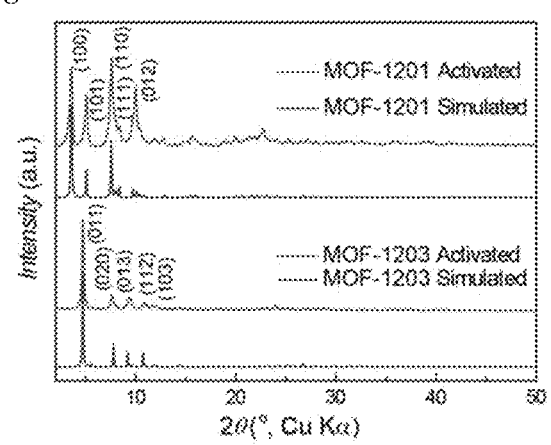
FIG. 3b. Powder X-ray patterns of activated (solvent-free) MOF-1201 and 1203 samples compared with the simulated patterns from single crystal structures.
Figure 6:
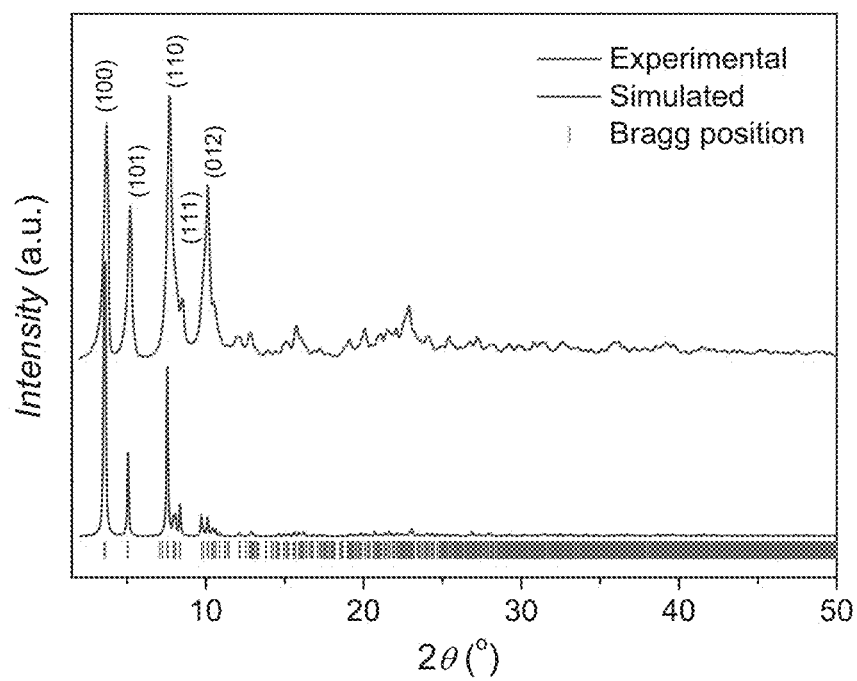
FIG. 6. Comparison of the experimental powder X-ray diffraction (PXRD) patterns of MOF-1201: activated (red) and simulated pattern (blue) from single crystal X-ray data.
Figure 7:
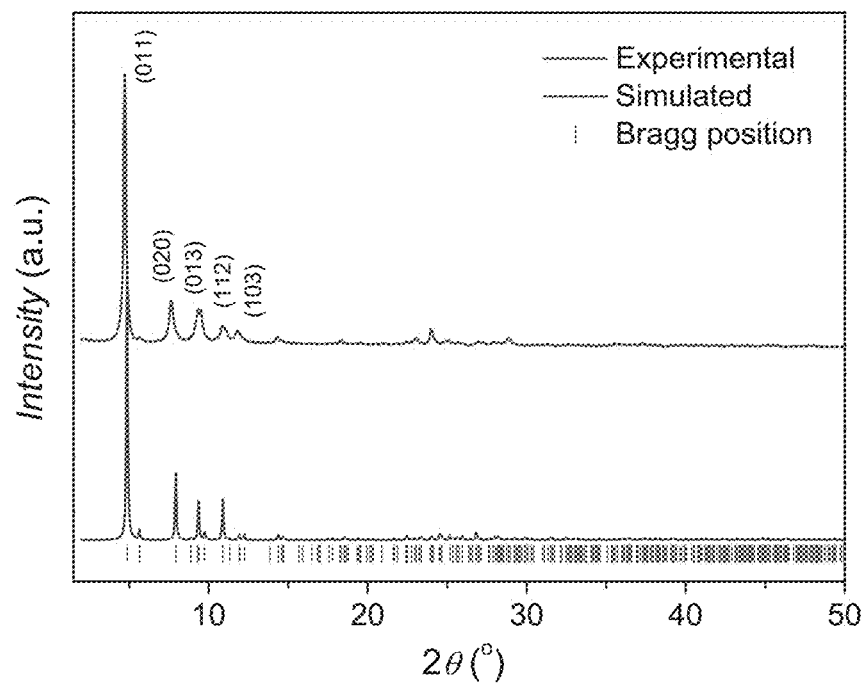
FIG. 7. Comparison of the experimental PXRD patterns of MOF-1203: activated (red) and simulated pattern (blue) from single crystal X-ray data.
Figure 8:
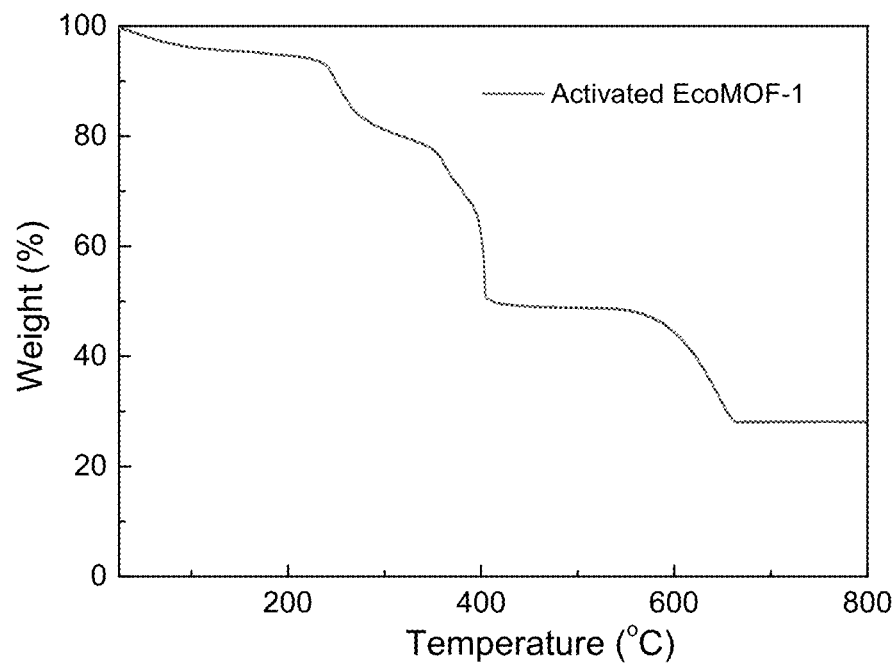
FIG. 8. Thermogravimetric analysis (TGA) trace for the activated sample of MOF-1201 in air.
Figure 9:
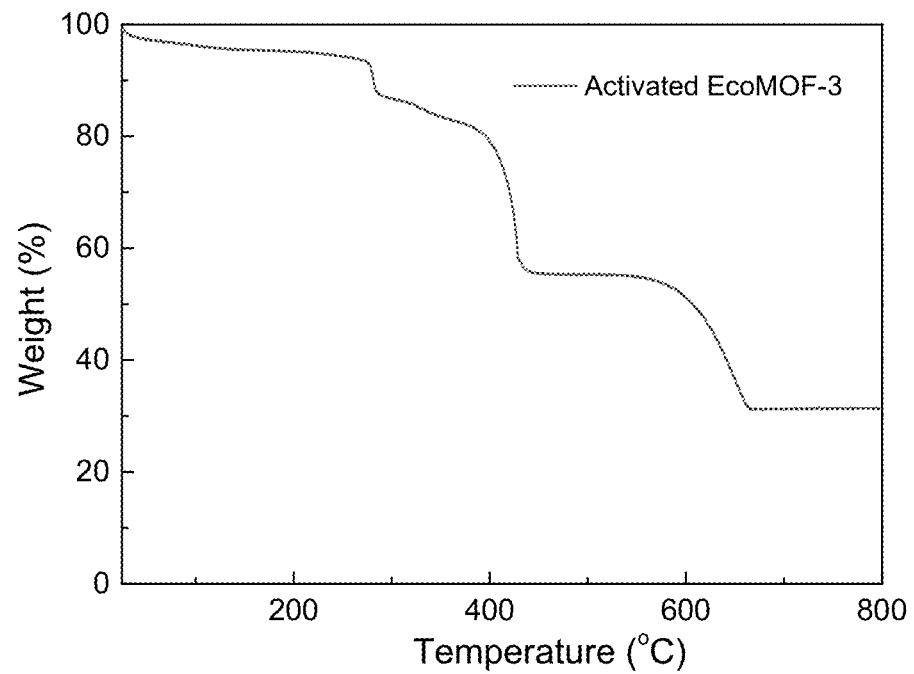
FIG. 9. TGA trace for the activated sample of MOF-1203 in air.

In FIG. 2b first column: asymmetric unit in MOF-1203 as shown in ball-and-stick diagram, ligands who partially connect to symmetry generated $Ca^{2+}$ centers are omitted for clarity; more than one bridge could exist for the same set of $Ca^{2+}$ centers; second column overall structures viewed along a axis represented in calcium oxide polyhedra. Asymmetric units are highlighted, and open channels are shown; right column, channels viewed along a axis (top) and [01$\bar{1}$] direction (bottom). Calcium oxide polyhedra belonging to aperture are highlighted. In color, as shown in priority application, C in black, O in red, Ca in cyan, $Ca^{2+}$ oxide polyhedra in cyan, H omitted for clarity Samples of MOF-1201 and MOF-1203 were solvent exchanged with ethanol (MOF-1201) and methanol (MOF-1203) for three days, followed by direct evacuation under dynamic vacuum (0.04 mbar) at room temperature for 12 hours to give solvent-free samples for the examination of the permanent porosity. Nitrogen sorption measurements at 77 K were then carried out. Both of the frameworks exhibited a fully reversible type I isotherm with steep $N_2$ uptake in the low-pressure regions ($P/P_0$<0.05) (FIG. 3a), indicating the permanent microporosity of these materials.[8] The Brunauer-Emmett-Teller (BET) surface areas[9] of MOF-1201 and MOF-1203 are estimated to be 430 and 160 $m^2$ $g^{-1}$ from $N_2$ isotherms. They possess pore volumes of 0.18 $cm^3$ $g^{-1}$ and 0.06 $cm^3$ $g^{-1}$, respectively, which are the same as those calculated from single crystal structures using PLATON.[19] Crystallinity of the solvent-free samples were then checked with powder X-ray diffraction (PXRD). The obtained powder patterns are in good agreement with the diffraction patterns simulated from the single crystal structures, confirming structural integrity upon activation and the phase purity of the bulk materials (FIG. 3b, FIGS. 6-7).

The porosity of MOF-1201 along with its eco-friendly compositions: $Ca^{2+}$, lactate, and acetate, allowed us to explore the potential application of metal-organic framework materials in agriculture and food industry, where the non-toxicity and human and environmental benignity are the most important requirements for a material to be used.[4,5] Here we've demonstrated the use of MOF-1201 as a solid formulation for volatile liquid fumigants.

Fumigants are one of the most important family of pesticides, which are widely used to prevent plants, especially these of high-value (e.g. strawberries and tomatoes), from soil-borne diseases to improve the quality and yield.[11] Two volatile liquid compounds, 1,3-dichloropropene (cis- and trans-mixtures) and chloropicrin, have been the most widely used fumigants with a large quantity being consumed each year.[11-12] Indeed, a pesticide use report published by California Department of Pesticide Regulations (CDPR) indicates the use of 1,3-dichloropropene and chloropicrin have achieved $5.99 \times 10^6$ kg and $4.08 \times 10^6$ kg respectively in California in 2014, ranking the $3^{rd}$ and $5^{th}$ of the all pesticides being used.[13]

Commercial formulations for the 1,3-dichloropropene or chloropicrin rely on the liquid forms applied by shank injection or by drip irrigation.[14] However, the direct use of liquids requires high dosage, which causes substantial air and groundwater pollution due to the high volatility and mobility of the liquid chemicals, as well as significant safety hazards to workers during handling and transporting.[11, 14-15] As a result of these adverse effects, the use of these chemicals are highly regulated, with both personal protective equipment and a buffer zone required.

Sorption based formulations using porous solids to adsorp fumigants and then slow release have emerged as an alternative to suppress the volatility, and toxicity of the chemicals as well as reduce pollutions.[16] Porous matrices such as activated carbon, activated clay, adsorption resin, and activated alumina have been proposed and shown prolonged effective lifetime of fumigants,[16] however, none of these carrier materials are naturally degradable, which greatly increases their environmental impact due to accumulation after implementation.

Figure 3C:
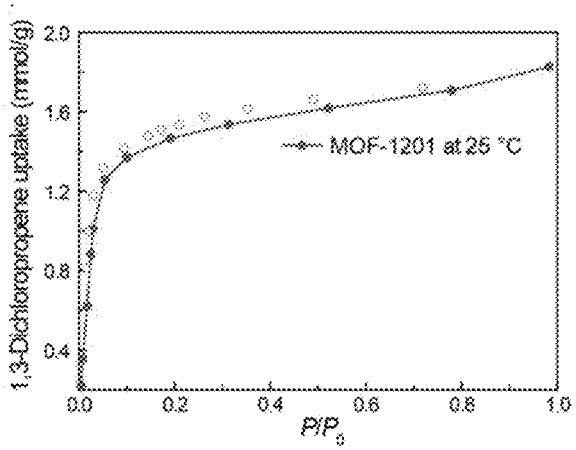
FIG. 3c. cis-1,3-dichloropropene vapor adsorption isotherm in MOF-1201 at 25° C., solid and open circles represent the adsorption and desorption branches, respectively.
Figure 3D:
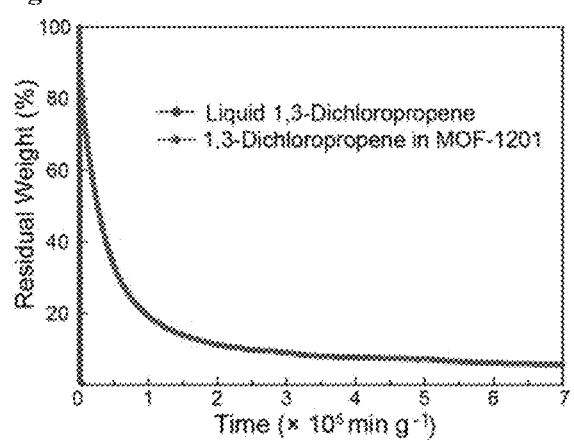
FIG. 3d. Slow release traces of pure liquid and MOF-1201 encapsulated cis-1,3-dichloropropene at 25° C.
Figure 4:
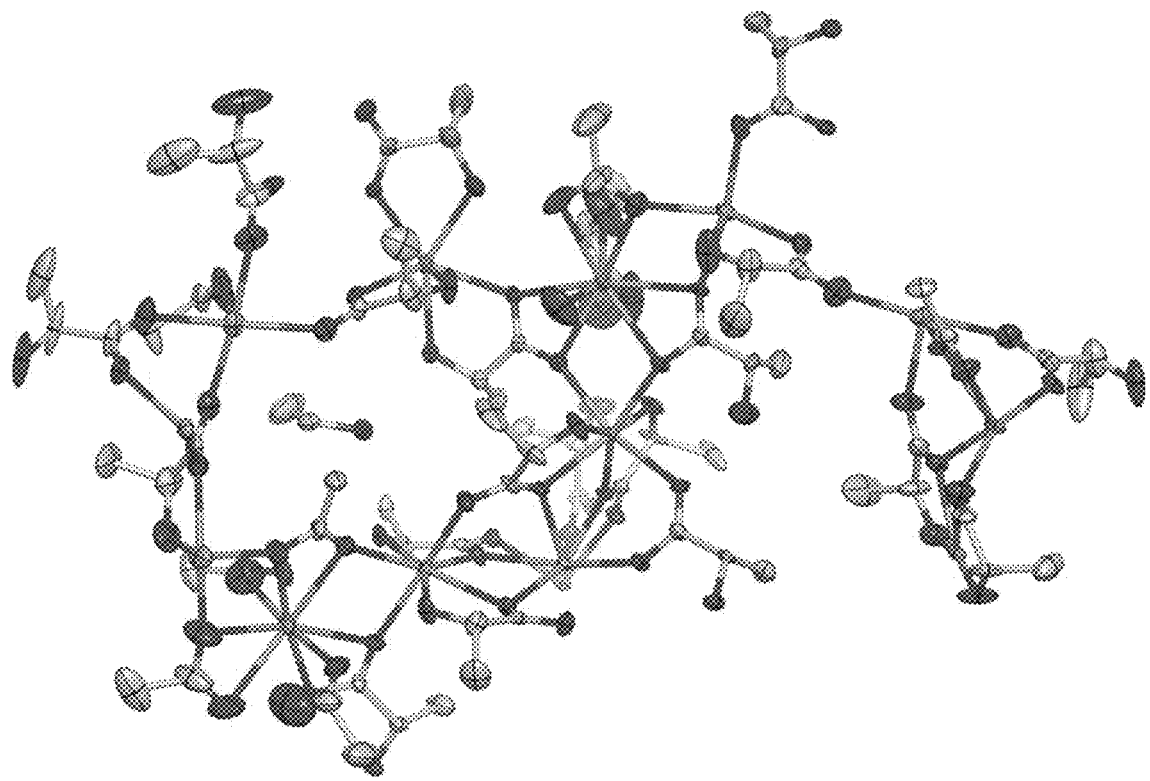
FIG. 4. Asymmetric unit in the single-crystal structure of MOF-1201 (thermal ellipsoids with 30% probability). Hydrogen atoms are omitted for clarity. Color scheme: C, grey; O, red; Ca, blue.
Figure 5:
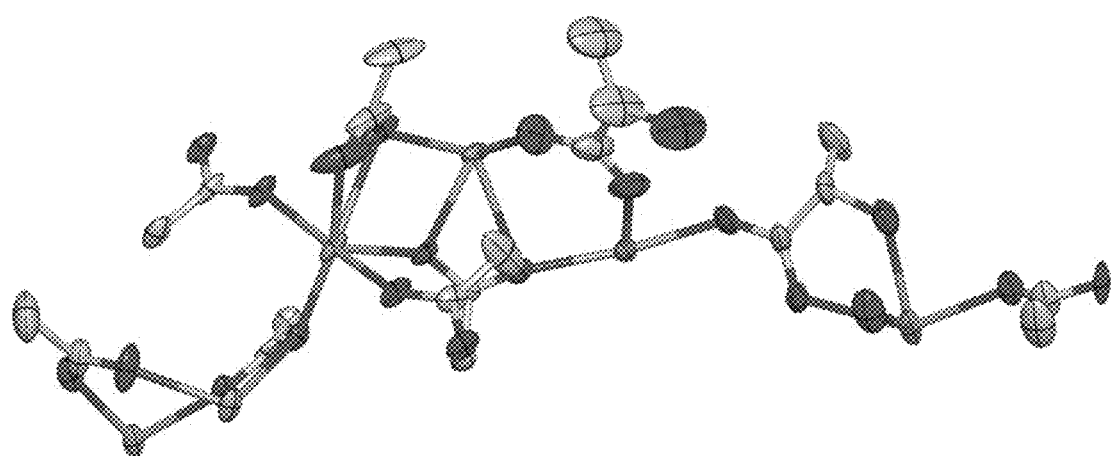
FIG. 5. Asymmetric unit in the single-crystal structure of MOF-1203 (thermal ellipsoids with 30% probability). Hydrogen atoms are omitted for clarity. Color scheme: C, grey; O, red; Ca, blue.

Here we present the use of MOF-1201 for this purpose Fumigant cis-1,3-dichloropropene has been chosen as an example. Static adsorption isotherm of cis-1,3-dichloropropene in MOF-1201 at 25° C. is shown in FIG. 3c, displaying a sharp uptake of 1.4 mmol $g^{-1}$ (13 wt %) in low partial pressure range ($P/P_0$=0.1), attributed to adsorption within the micropores. This uptake was in the range of the values achieved in other porous materials (5-40 wt %).[16d] Preliminary slow release performance was demonstrated in lab by purging the sample of cis-1,3-dichloropropene loaded MOF-1201 or liquid cis-1,3-dichloropropene in an air flow of 1.0 $cm^3$ $min^{-1}$ and the sample weight was monitored by thermogravimetric instrument. As shown in FIG. 3d, liquid cis-1,3-dichloropropene released quickly, with 80% of the total weight evaporated within 1,000 min $g^{-1}$. In contrast, the cis-1,3-dichloropropene encapsulated in MOF-1201 released in a much slower manner, with 80% of the total (10.5 wt %) released in 100,000 min $g^{-1}$, corresponding to 100 times slower compared with liquid cis-1,3-dichloropropene under the same conditions.

Figure 10:
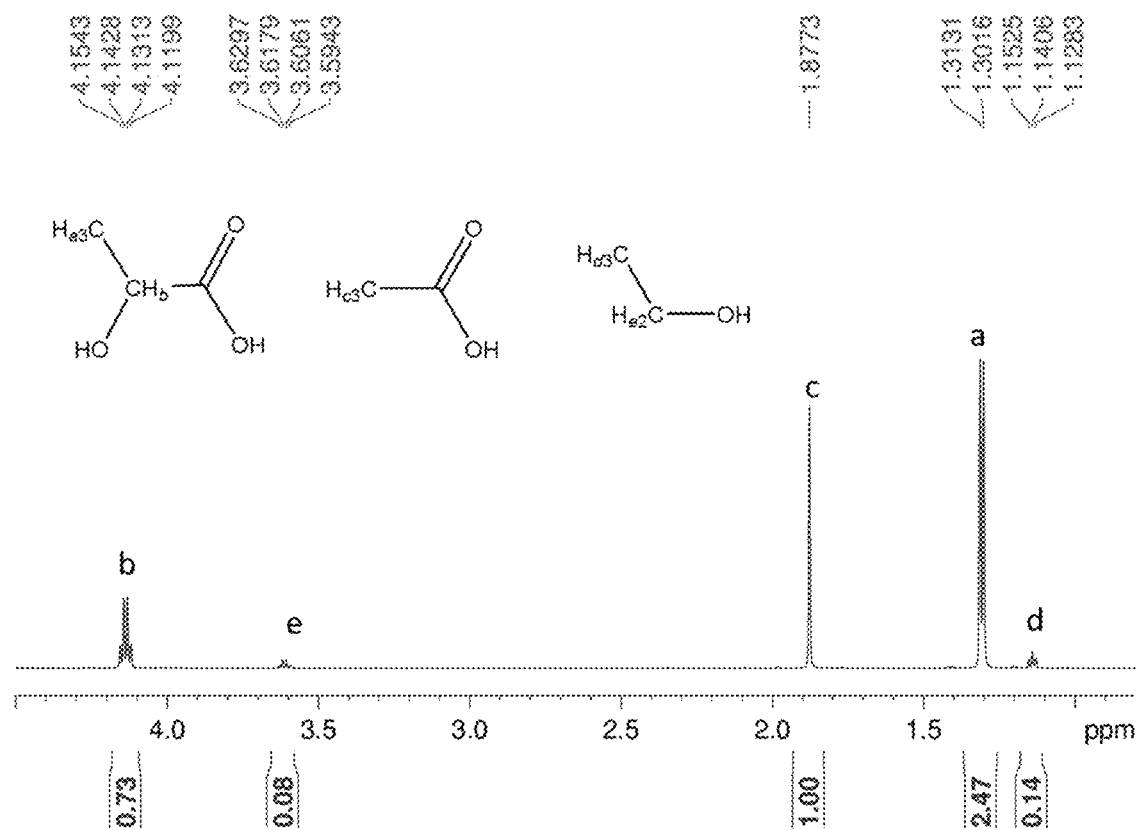
FIG. 10. $^1$H-NMR spectrum of solution of MOF1201.
Figure 11:
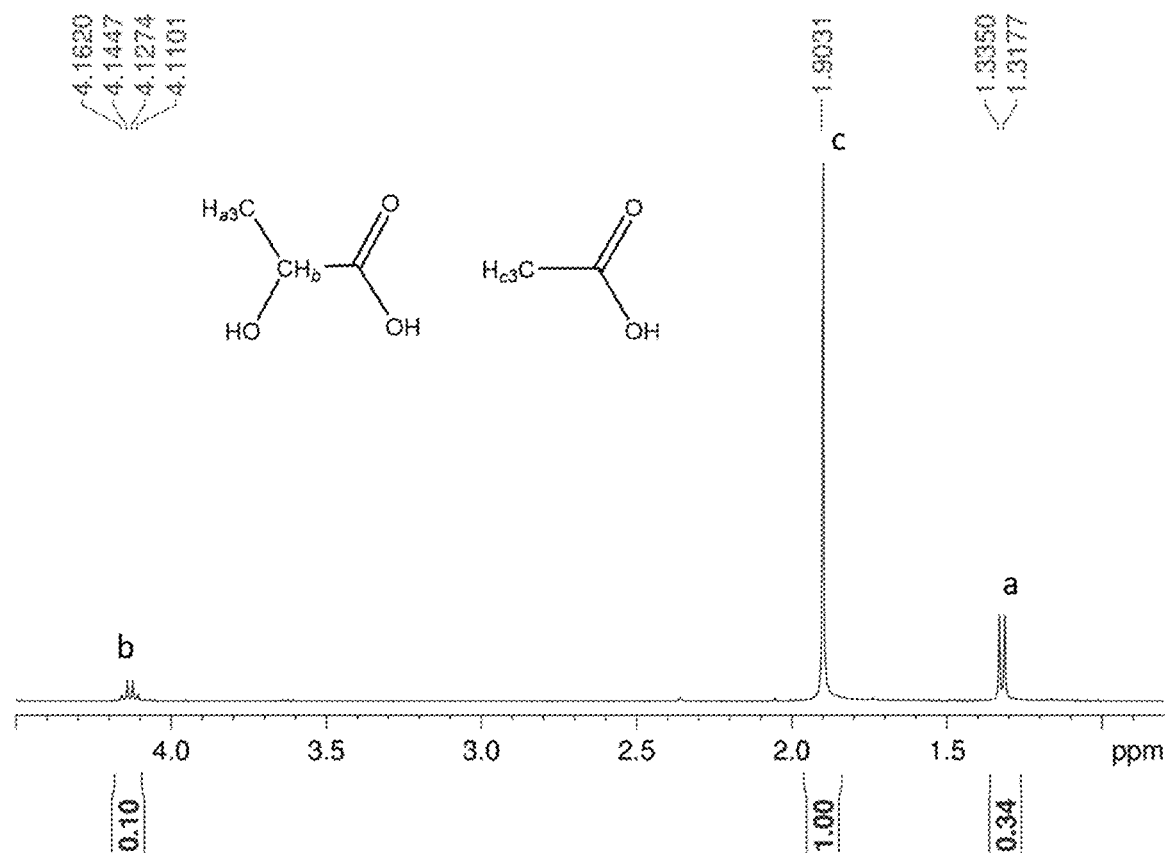
FIG. 11. $^1$H-NMR spectrum of solution of MOF-1203.
Figure 12:
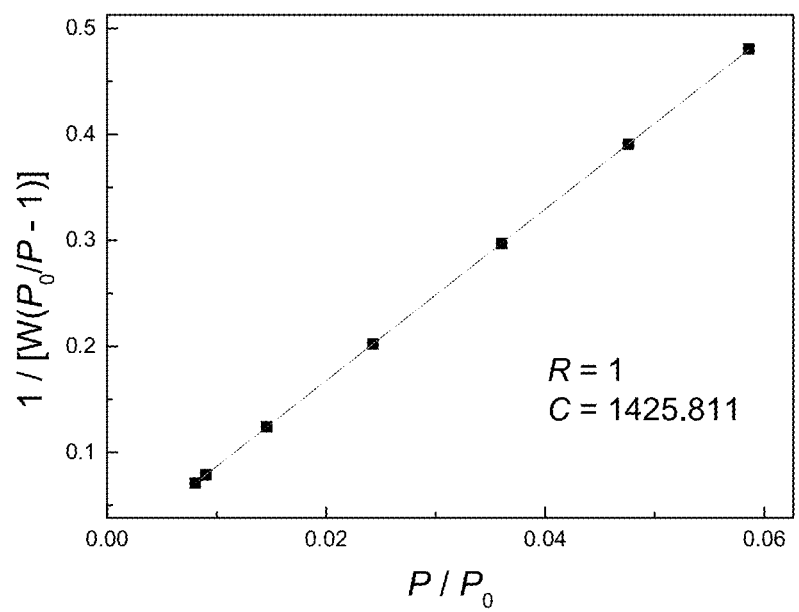
FIG. 12. Multiple point Brunauer-Emmett-Teller (BET) plot of MOF-1201 giving a specific surface area of 430 $m^2/g$.
Figure 13:
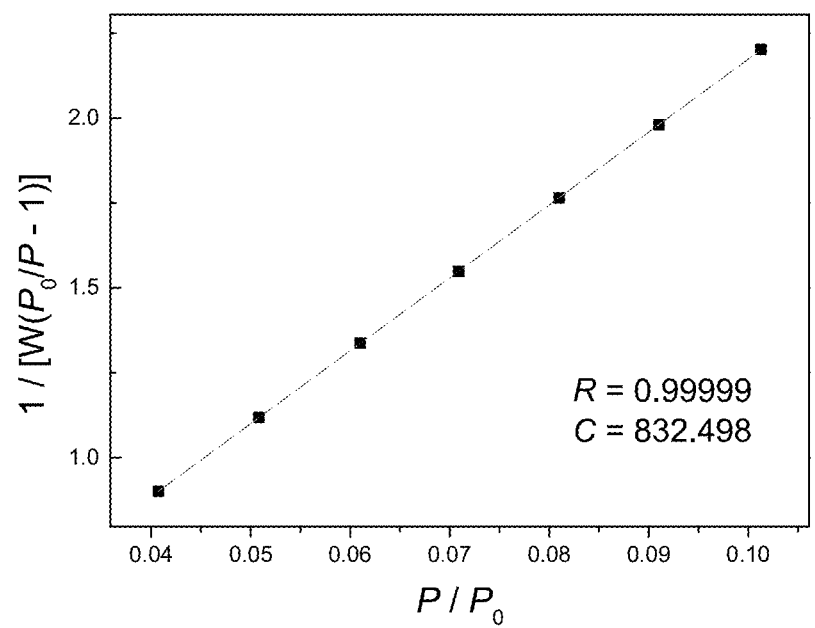
FIG. 13. Multiple point BET plot of MOF-1203 giving a specific surface area of 162 $m^2/g$.

The degradability of MOF-1201 was then tested. MOF-1201 can be easily dissolved in water to give its eco-friendly components: $Ca^{2+}$ ions, lactate, and acetate (FIG. 10). It is found that 1 L water can dissolve 120±10 g of MOF-1201, and the saturated solution has a nearly neutral pH value (7.6). This property allows MOF-1201 the potential to overcome the accumulation issues within other porous materials, thus minimize adverse effects to the environment but leaving fertilizer (calcium) to the soil.[17]

To conclude, we have demonstrated the first examples of eco-friendly $Ca^{2+}$ MOFs constructed from non-toxic, renewable lactate linkers. We further demonstrated the use of MOF-1201 as a degradable carriers. Our results demonstrate both the creation of eco-friendly Ca MOFs and their use in agriculture.

REFERENCES (1) (a) Yaghi, O. M.; O'Keeffe, M.; Ockwig, N. W.; Chae, H. K.; Eddaoudi, M.; Kim, J. Nature 2003, 423, 705-714. (b) Kaskel, S. The Chemistry of Metal-Organic Frameworks: Synthesis, Characterization, and Applications; Wiley-VCH: Weinheim, 2016.
(2) Furukawa, H.; Cordova, K. E.; O'Keeffe, M.; Yaghi, O. M. Science 2013, 341, 1230444.
(3) (a) Schröder, M. Functional Metal-Organic Frameworks: Gas Storage, Separation and Catalysis; Springer: Berlin, 2010. (b) Li, J.-R.; Sculley, J.; Zhou, H.-C. Chem. Rev. 2012, 112, 869-932.
(4) Forgan, R. S. Metal-Organic Frameworks: Edible Frameworks. Encyclopedia of Inorganic and Bioinorganic Chemistry; John Wiley & Sons: New York, 2014.
(5) Imaz, I.; Rubio-Martínez, M.; An, J.; Solé-Font, I.; Rosi, N. L.; Maspoch, D. Chem. Comm. 2011, 47, 7287-7302.
(6) Fromm, K. M. Coord. Chem. Rev. 2008, 252, 856-885.
(7) National Library of Medicine. Toxicology Data Network. https://[bracket inserted to inactivate hyperlink]

toxnet.nlm nih.gov/index.html. Both calcium lactate and calcium acetate are generally recognized as safe (GRAS) as food additive.
(8) Thommes, M.; Kaneko, K.; Neimark, A. V.; Olivier, J.; Rodriguez-Reinoso, F.; Rouquerol, J.; Sing, K. S. Pure and Appl. Chem. 2015, 87, 1051-1069.
(9) Walton, K. S.; Snurr, R. Q. J. Am. Chem. Soc. 2007, 129, 8552-8556.
(10) Spek, A. L. Acta Cryst. 2009, D65, 148-155.
(11) (a) Shorter, J. H.; Kolb, C. E.; Crill, P. M.; Kerwin, R. A. Nature 2002, 377, 717-719. (b) Martin, F. N. Annu. Rev. Phytopathol. 2003, 41, 325-350.
(12) Ashworth, D. J.; Yates, S. R.; Wesenbeeck, I. J. V.; Stanghellini, M. J. Agric. Food Chem. 2015, 63, 415-421.
(13) Pesticide Use reporting-2014 Summary Data, Sacramento, CA, USA, 2014; available at http://www[bracket inserted to inactivate hyperlink].cdpr.ca.gov/docs/pur/purl4rep/14_pur.htm.
(14) Kim, J.-H.; Papiernik, S. K.; Farmer, W. J.; Gan, J.; Yates, S. R. J. Environ. Qual. 2003, 32, 2223-2229.
(15) (a) Yates, S. R.; Ashworth, D. J.; Zheng, W.; Zhang, Q.; Knuteson, J.; Wessenbeeck, I. J. V. J. Agric. Food Chem. 2015, 63, 5354-5363. (b) Desaeger, J. A. Eger, J. E. J.; Csinos, A. S.; Gilreath, J. P.; Olson, S. M.; Webster, T. M. Pest Manag. Sci. 2004, 60, 1220-1230.
(16) (a) Akira, S.; Mizuyoshi, F.; Hiroshi, A.; Shiyunnosuke, W.; Nobuji, T. Granular chloropicrin preparation for soil disinfection and production thereof. Japan. Patent JPH01172302 (A), Jul. 7, 1989. (b) Solar, J. M.; Wilson, C. L.; Ghaouth, A. E. Controlled release fumigation of harvested agricultural commodities. U.S. Pat. No. 5,958,490 A, Sep. 28, 1999. (c) Han, J. L. Mixed solid preparation of chloropicrin and 1.3-dichloropropylene and manufacturing technology thereof. China Patent CN 101627754 B, Nov. 13, 2013. (d) Han, J. L.; Yi, C. J. Preparation method and application of 1,3-dichloropropene solid slow-release preparation. China Pat. Appl. CN 201310062631, May 22, 2013.
(17) Engelstad, O. P. Fertilizer Technology and Use; Soil Science Society of America: Madison, 1985.

SYNTHETIC PROCEDURES

Calcium acetate monohydrate $(Ca(OAc)_2 \cdot H_2O)$, L-(+)-Lactic acid, anhydrous methanol and ethanol were purchased from commercial source and were used directly without further purification. All the synthetic procedures were conducted in air. The MOFs were activated by the following procedure: As-synthesized MOFs were washed with fresh anhydrous ethanol (MOF-1201) and methanol (MOF-1203) for 1 day, six times per day. The samples were then evacuated to remove guest molecules under vacuum (0.01 Torr) at ambient temperature for 12 hrs. The following measurements were conducted using the activated samples for MOFs unless otherwise noted.

Elemental analysis (EA) of activated MOF-1201 and -3 were performed using a Perkin Elmer 2400 Series II CHNS elemental analyzer; $^1H$ NMR spectra on digested solutions of MOFs were acquired on a Bruker AVB-400 NMR spectrometer, with chemical shifts of linkers identified by comparing with spectra for each pure linker. Samples (ca. 10 mg for each) were dissolved in $D_2O$ (600 µL) with sonication; Attenuated-total-reflectance Fourier-transform infrared (ATR-FTIR) spectra of neat ZIFs were recorded on a Bruker ALPHA Platinum ATR-FTIR Spectrometer.

MOF-1201, $Ca_{14}$(L-lactate)$_{20}$(Acetate)$_8$(EtOH)($H_2O$). 0.071 g calcium acetate monohydrate $(Ca(OAc)_2 \cdot H_2O, 0.4$ mmol), and 0.072 g L-(+)-Lactic acid (HL, 0.8 mmol) were mixed in 6 mL anhydrous ethanol in a 23 mL Teflon autoclave. The autoclave was then sealed and heated in 120° C. isothermal oven for 4 days. After cooling down to room temperature, the crystals were washed with anhydrous ethanol for 1 day. (Yield: 26% based on Ca). EA: Calcd. for $Ca_{14}(C_3H_5O_3)_{20}(C_2H_3O_2)_8(C_2H_6O)(H_2O)$: C, 32.54; H, 4.62. Found: C, 31.67; H, 4.75. ATR-FTIR (4000-400 cm$^{-1}$): 3250(br), 2979(w), 1563(s), 1422(s), 1314(m), 1267(m), 1122(s), 1089(w), 1044(m), 930(w), 858(m), 773(m), 664(m), 616(m), 550(m), 469(w), 442(w), 423(w).

MOF-1203, $Ca_6$(L-lactate)$_3$(Acetate)$_9$($H_2O$). 0.071 g calcium acetate monohydrate $(Ca(OAc)_2 \cdot H_2O, 0.4$ mmol), and 0.036 g L-(+)-Lactic acid (HL, 0.4 mmol) were mixed in 6 mL anhydrous methanol in a 23 mL Teflon autoclave. The autoclave was then sealed and heated in 100° C. isothermal oven for 3 days. After cooling down to room temperature, the crystals were washed with anhydrous methanol for 1 day. (Yield: 25% based on Ca). EA: Calcd. for $Ca_6(C_3H_5O_3)_3$ $(C_2H_3O_2)_9$: C, 30.68; H, 4.20. Found: C, 31.33; H, 4.07. ATR-FTIR (4000-400 cm$^{-1}$): 3300(br), 2981(w), 1540(s), 1462(s), 1417(s), 1320(w), 1271(m), 1138(m), 1123(m), 1051(w), 1024(m), 956(w), 934(w), 860(m), 774(m), 662(s), 649(m), 617(s), 561(m), 468(m), 419(w).

Single crystal X-ray diffraction (SXRD) data was collected for both MOFs using as-synthesized crystals. Data for MOF-1201 and -3 were collected at beamline 11.3.1 of the ALS at LBNL, equipped with a Bruker Photon 100 CMOS area detector using synchrotron radiation (10-17 KeV), at 0.7749(1) Å. Samples were mounted on MiTeGen® kapton loops and placed in a 100(2) K nitrogen cold stream.

Data were processed with the Bruker APEX2 software package (AXS Inc., Madison, Wis., 2010; Sheldrick, G. M. Acta Cryst. A 2008, 64, 112-122), integrated using a program trademarked SAINT v8.34A and corrected for the absorption by SADABS 2014/4 routines (no correction was made for extinction or decay). The structures were solved by intrinsic phasing using a program trademarked SHELXT, and refined by full-matrix least squares on $F^2$ using a program trademarked SHELXL-2014. All non-hydrogen atoms were refined anisotropically. Hydrogen atoms were geometrically calculated and refined as riding atoms unless otherwise noted. In both structures, highly disordered guest molecules occupying the cavities of the structure, which could not be modeled and so were accounted for using solvent masking using the Olex2 software package (Dolomanov, et al. Appl. Cryst. 2009, 42, 339-341; Rees, et al. Acta Cryst. D 2005, 61, 1299-13)

MOF-1201. A colorless rod-shaped (100 µm×20 µm×20 µm) crystal of as-synthesized MOF-1201 was quickly picked up from the mother liquor, and placed in paratone oil to minimize crystal degradation, and mounted at beamline 11.3.1 at the ALS using radiation at λ=0.7749(1) Å at 100 K.

TABLE S1

Crystal data and structure determination for MOF-1201

| Compound | MOF-1201 |
|---|---|
| Chemical formula | $C_{76}H_{127}O_{76}Ca_{14}$ |
| Formula mass | 2817.89 |
| Crystal system | monoclinic |
| Space group | $P2_1$ |
| λ (Å) | 0.7749 (1) |
| a (Å) | 24.3868 (11) |
| b (Å) | 13.2612 (6) |
| c (Å) | 24.9710 (10) |

TABLE S1-continued

Crystal data and structure determination for MOF-1201

| Compound | MOF-1201 |
|---|---|
| β (°) | 90.327 (2) |
| Z | 2 |
| V (Å$^3$) | 8075.4 (6) |
| Temperature (K) | 100 (2) |
| Size/mm$^3$ | 0.1 × 0.02 × 0.02 |
| Density (g/cm$^{-3}$) | 1.159 |
| Measured reflections | 119229 |
| Unique reflections | 29436 |
| Parameters | 1544 |
| Restraints | 265 |
| $R_{int}$ | 0.0723 |
| θ range (°) | 2.10-27.89 |
| $R_1$, $wR_2$ | 0.0621, 0.1772 |
| S (GOF) | 1.076 |
| Max/min res. dens. (e/Å$^3$) | 0.60/−0.33 |
| Flack parameter | 0.150 (10) |

$^a R_1 = \Sigma ||F_o| - |F_c||/\Sigma |F_o|$; $^b wR_2 = [\Sigma w(F_o^2 - F_c^2)^2 / \Sigma w(F_o^2)^2]^{1/2}$; $^c S = [\Sigma w(F_o^2 - F_c^2)^2 / (N_{ref} - N_{par})]^{1/2}$.
MOF-1203. A colorless needle-shaped (90 μm × 90 μm × 5 μm) crystal of as-synthesized MOF-1203 was quickly picked up from the mother liquor and mounted at beamline 11.3.1 at the ALS using radiation at λ = 0.7749 (1) Å.

TABLE S2

Crystal data and structure determination for MOF-1203

| Compound | MOF-1203 |
|---|---|
| Chemical formula | C$_{40}$H$_{59.33}$O$_{40.67}$Ca$_9$ |
| Formula mass | 1551.64 |
| Crystal system | orthorhombic |
| Space group | I2$_1$2$_1$2$_1$ |
| λ (Å) | 0.7749 (1) |
| a (Å) | 10.5046 (4) |
| b (Å) | 22.2580 (9) |
| c (Å) | 31.2485 (13) |
| Z | 4 |
| V (Å$^3$) | 7306.3 (5) |
| Temperature (K) | 100 (2) |
| Size/mm$^3$ | 0.09 × 0.005 × 0.005 |
| Density (g/cm$^{-3}$) | 1.411 |
| Measured reflections | 7620 |
| Unique reflections | 3865 |
| Parameters | 433 |
| Restraints | 59 |
| $R_{int}$ | 0.1195 |
| θ range (°) | 2.23-22.86 |
| $R_1$, $wR_2$ | 0.0524, 0.1406 |
| S (GOF) | 1.026 |
| Max/min res. dens. (e/Å$^3$) | 0.60/−0.33 |
| Flack parameter | 0.09 (3) |

$^a R_1 = \Sigma ||F_o| - |F_c||/\Sigma |F_o|$; $^b wR_2 = [\Sigma w(F_o^2 - F_c^2)^2 / \Sigma w(F_o^2)^2]^{1/2}$; $^c S = [\Sigma w(F_o^2 - F_c^2)^2 / (N_{ref} - N_{par})]^{1/2}$.

Powder X-ray diffraction (PXRD) analysis were conducted on a Bruker D8 Advance diffractometer with Cu K$_\alpha$ radiation (λ=1.54056 Å). Phase purity of the materials is examined by comparing experimental and simulated PXRD patterns.

Thermogravimetric analysis (TGA) curves were recorded using a TA Q500 thermal analysis system under air flow.

Fumigant adsorption and slow release measurements. cis-1,3-dichloropropene vapor sorption isotherm at 25° C. were measured in-house on a BEL Japan BELSORP-aqua3. Prior to measurements, the analyte was flash frozen in liquid nitrogen and then evacuated under dynamic vacuum at least twice to remove any gases from the reservoir. The measurement temperature was controlled and monitored with a water bath held at 25° C. Helium was used to estimate dead space for vapor adsorption measurements.

Slow release experiments were carried out using the TA Q500 thermal analysis system under constant air flow rate of 1 cm$^3$ min$^{-1}$.

The invention claimed is:

1. A Ca$^{2+}$-based metal-organic framework (MOF) composition comprising chelating L-lactate and acetate, the MOF of formula: [Ca$_{14}$(L-lactate)$_{(16-24)}$ (Acetate)$_{(12-4)}$] or [Ca$_6$(L-lactate)$_{(2-4)}$ (acetate)$_{(10-8)}$], wherein the lactate and acetate sum to 28 and 12, respectively.

2. The composition of claim 1, wherein the MOF is of formula: [Ca$_{14}$(L-lactate)$_{(16-24)}$ (acetate)$_{(12-4)}$], wherein the lactate and acetate sum to 28.

3. The composition of claim 1, wherein the MOF is of formula: [Ca$_{14}$(L-lactate)$_{(18)}$ (acetate)$_{(10)}$].

4. The composition of claim 1, wherein the MOF is of formula: [Ca$_{14}$(L-lactate)$_{(21)}$ (acetate)$_{(7)}$].

5. The composition of claim 1, wherein the MOF is of formula: [Ca$_6$(L-lactate)$_{(2-4)}$ (acetate)$_{(10-8)}$], wherein the lactate and acetate sum to 12.

6. The composition of claim 1, wherein the MOF is of formula: [Ca$_6$(L-lactate)$_{(4)}$ (acetate)$_{(8)}$].

7. The composition of claim 1, wherein the MOF is of formula: [Ca$_6$(L-lactate)$_{(2.5)}$ (acetate)$_{(9.5)}$].

8. The composition of claim 1, wherein the MOF is of formula: [Ca$_{14}$(L-lactate)$_{(20)}$ (acetate)$_{(8)}$].

9. The composition of claim 1, wherein the MOF is of formula: [Ca$_6$(L-lactate)$_{(3)}$ (acetate)$_{(9)}$].

10. The composition of claim 1 further comprising an agent encapsulated in the MOF, wherein the agent is a fumigant cis-1,3-dichloropropene.

11. The composition of claim 8 further comprising an agent encapsulated in the MOF, wherein the agent is a fumigant cis-1,3-dichloropropene.

12. The composition of claim 9 further comprising an agent encapsulated in the MOF, wherein the agent is a fumigant cis-1,3-dichloropropene.

13. The composition of claim 10, wherein the MOF is of formula selected from: [Ca$_{14}$(L-lactate)$_{(18)}$ (acetate)$_{(10)}$], [Ca$_{14}$(L-lactate)$_{(21)}$ (acetate)$_{(7)}$], [Ca$_6$(L-lactate)$_{(4)}$ (acetate)$_{(8)}$], [Ca$_6$(L-lactate)$_{(2.5)}$ (acetate)$_{(9.5)}$], [Ca$_{14}$(L-lactate)$_{(20)}$ (acetate)$_{(8)}$], and [Ca$_6$(L-lactate)$_{(3)}$ (acetate)$_{(9)}$].

14. The composition of claim 1 comprising a solid formulation of a volatile liquid fumigant cis-1,3-dichloropropene, wherein the fumigant is encapsulated in the MOF and the MOF is of formula: [Ca$_{14}$(L-lactate)$_{(20)}$ (acetate)$_{(8)}$].

15. The composition of claim 1 comprising a solid formulation of a volatile liquid fumigant cis-1,3-dichloropropene, wherein the fumigant is encapsulated in the MOF and the MOF is of formula: [Ca$_6$(L-lactate)$_{(3)}$ (acetate)$_{(9)}$].

16. A method of using the composition of claim 1, the method comprising the steps of:
 (a) providing the composition in a non-toxic, biodegradable carrier, wherein the composition further comprises cis-1,3-dichloropropene encapsulated in the MOF, and
 (b) delivering the composition in the carrier by fumigation or spray.

17. A method of using the composition of claim 8, the method comprising the steps of:
 (a) providing the composition in a non-toxic, biodegradable carrier, wherein the composition further comprises cis-1,3-dichloropropene encapsulated in the MOF, and
 (b) delivering the composition in the carrier by fumigation or spray.

18. A method of using the composition of claim 9, the method comprising the steps of:

(a) providing the composition in a non-toxic, biodegradable carrier, wherein the composition further comprises cis-1,3-dichloropropene encapsulated in the MOF, and
(b) delivering the composition in the carrier by fumigation or spray.

* * * * *